United States Patent
Takizawa

(10) Patent No.: US 8,449,454 B2
(45) Date of Patent: May 28, 2013

(54) CAPSULE ENDOSCOPE SYSTEM

(75) Inventor: Hironobu Takizawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/761,826

(22) Filed: Apr. 16, 2010

(65) Prior Publication Data

US 2010/0268026 A1 Oct. 21, 2010

Related U.S. Application Data

(63) Continuation of application No. PCT/JP2009/068148, filed on Oct. 21, 2009.

(30) Foreign Application Priority Data

Oct. 24, 2008 (JP) ................................ 2008-274737

(51) Int. Cl.
*A61B 1/04* (2006.01)
*A61B 1/06* (2006.01)
*A61B 5/05* (2006.01)

(52) U.S. Cl.
USPC .......... 600/117; 600/109; 600/118; 600/160; 600/178; 600/424

(58) Field of Classification Search
USPC ................. 600/101, 109, 117, 118, 415, 424
See application file for complete search history.

(56) References Cited

U.S. PATENT DOCUMENTS

| | | | |
|---|---|---|---|
| 5,681,260 A | 10/1997 | Ueda et al. | |
| 2006/0224063 A1* | 10/2006 | Segawa et al. | 600/424 |
| 2007/0185381 A1 | 8/2007 | Kimoto et al. | |
| 2007/0221233 A1 | 9/2007 | Kawano et al. | |
| 2007/0265496 A1* | 11/2007 | Kawano et al. | 600/109 |
| 2008/0035521 A1 | 2/2008 | Takizawa et al. | |
| 2008/0300453 A1 | 12/2008 | Aoki et al. | |

FOREIGN PATENT DOCUMENTS

| | | |
|---|---|---|
| DE | 10 2005 032 373 A1 | 12/2006 |
| JP | 55-133237 | 10/1980 |
| JP | 4-8343 | 1/1992 |
| JP | 2005-40400 | 2/2005 |
| JP | 2005-185544 | 7/2005 |
| JP | 2006-68501 | 3/2006 |

(Continued)

OTHER PUBLICATIONS

Decision of a Patent Grant dated Oct. 19, 2010 with English translation.
International Search Report dated Jan. 19, 2010.
European Search Report dated Feb. 20, 2013 from corresponding European Patent Application No. 09 82 2054.4.

*Primary Examiner* — Philip R Smith
*Assistant Examiner* — Rynae Boler
(74) *Attorney, Agent, or Firm* — Scully Scott Murphy & Presser, PC

(57) ABSTRACT

A capsule endoscope system includes a contact detector that detects contact with an inner wall of a lumen in the subject; a magnet which is equipped in the capsule endoscope; a magnetic field generating device that is provided at a position, which is fixed with respect to the magnet, and generates a guidance magnetic field to apply to the magnet from the outside of the subject; and a magnetic field generation controller that performs control for guidance in a direction in which the capsule endoscope moves, which is the direction of the axis of the lumen, and performs guidance control for separating the capsule endoscope from the inner wall of the lumen based on a result of detection by the contact detector.

13 Claims, 10 Drawing Sheets

FOREIGN PATENT DOCUMENTS

| JP | 2007-167214 | 7/2007 |
| WO | WO 2007/077768 A1 | 7/2007 |
| WO | WO 2007/077922 A1 | 7/2007 |
| WO | WO 2008/082005 A1 | 7/2008 |

* cited by examiner

CAPSULE ENDOSCOPE SYSTEM

CROSS-REFERENCE TO RELATED APPLICATIONS

This application is a continuation of PCT international application Ser. No. PCT/JP2009/068148 filed on Oct. 21, 2009 which designates the United States, incorporated herein by reference.

BACKGROUND OF THE INVENTION

1. Field of the Invention

The present invention relates to a capsule endoscope system that guides a capsule endoscope that is introduced into a subject and floats in liquid or is submerged in the liquid in the subject.

2. Description of the Related Art

In recent years, in the field of endoscopy, capsule body-insertable devices (for example, capsule endoscopes) have been proposed that are provided with an imaging function and a wireless communication function and body-insertable device systems have been developed that acquire in-vivo images of a subject by using the capsule endoscope. A capsule endoscope is, for example, swallowed by a patient in order to observe (examine) the inside of the subject. Thereafter, the capsule endoscope moves through the body cavity, such as the internal organs including the stomach and the small intestine, by peristalsis of the internal organs until the capsule endoscope is naturally discharged and functions to capture in-vivo images of the subject at intervals of, for example, 0.5 second.

While the capsule endoscope moves through the inside of the subject, images that are captured by the capsule endoscope are received by an external image display device via antennae that are arranged on the body surface of the subject. The image display device has a function for communicating with the capsule endoscope by wireless communication and an image memory function. The image display device sequentially stores the in-vivo images of the subject, which are received from the capsule endoscope, in a memory. A doctor or a nurse can observe (examine) the inside of the subject and diagnose the subject through display of the in-vivo images of the alimentary canal of the subject.

Japanese Laid-open Patent Publication No. 2005-185544 describes a capsule endoscope that moves using electric propulsion. A living tissue receives a localized electrical stimulus via an electrode. The capsule endoscope moves through a living body using the effects of the contraction of the electrically-stimulated living tissue. The capsule endoscope includes a force sensor that electrically detects whether the electrode, which is provided in the body of the capsule endoscope, and the living tissue have been brought into contact with each other. The capsule endoscope can be stably propelled because a current flows after it is checked, using the force censor, to determine whether the living tissue and the electrode have been brought into contact with each other.

SUMMARY OF THE INVENTION

A capsule endoscope system according to an aspect of the present invention is a capsule endoscope system for guiding a capsule endoscope that is introduced into a subject and floats in liquid or is submerged in the liquid in the subject. The capsule endoscope system includes a contact detector that detects contact with an inner wall of a lumen in the subject; a magnet which is equipped in the capsule endoscope; a magnetic field generating device that is provided at a position, which is fixed with respect to the magnet, and generates a guidance magnetic field to apply to the magnet from the outside of the subject; and a magnetic field generation controller that performs control for guidance in a direction in which the capsule endoscope moves, which is the direction of the axis of the lumen, and performs guidance control for separating the capsule endoscope from the inner wall of the lumen based on a result of detection by the contact detector.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Preferred embodiments of a capsule endoscope system according to the present invention will be explained in detail below with reference to the drawings. The present invention is not limited to these embodiments.

First Embodiment

Figure 1:
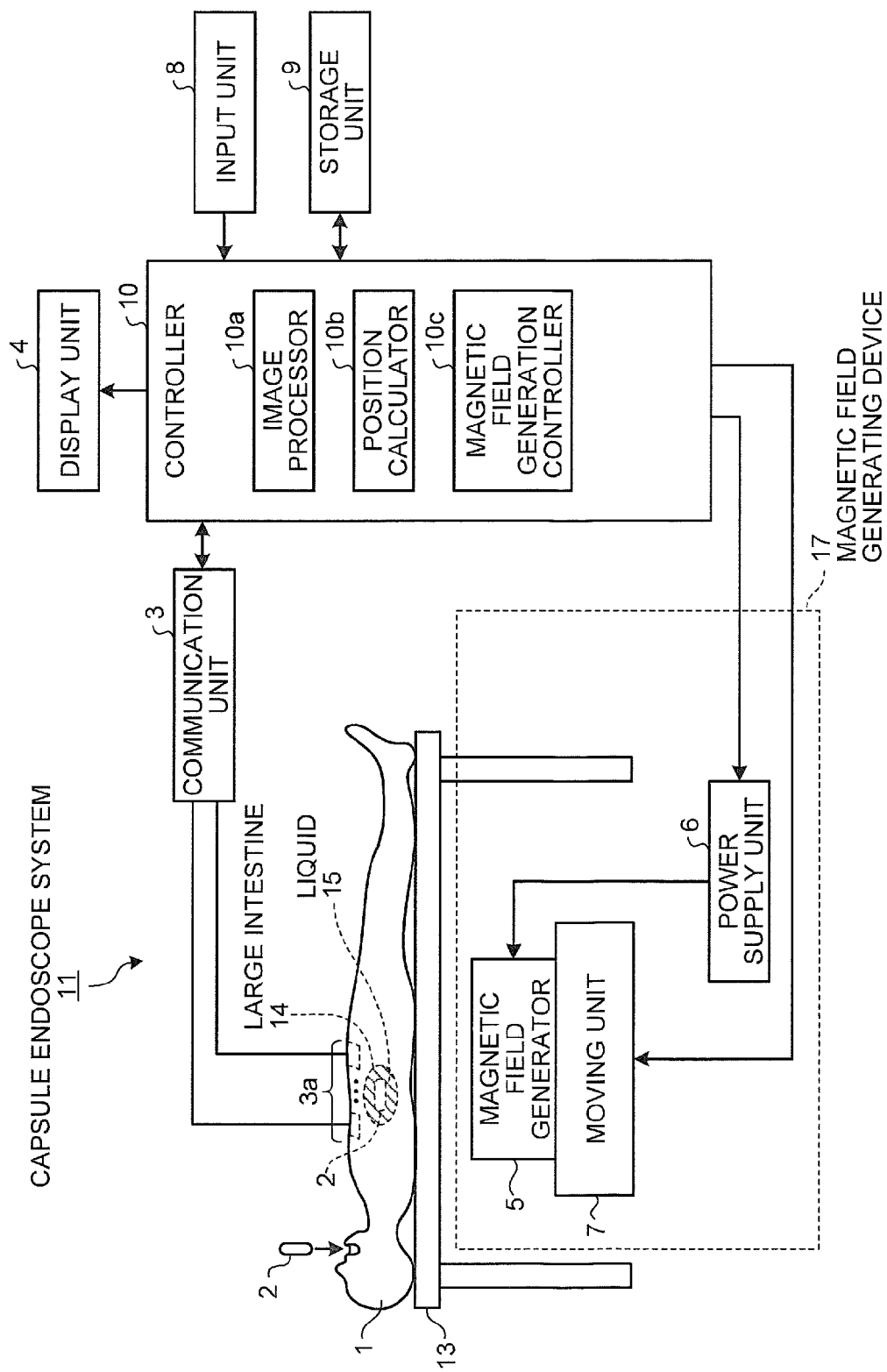
FIG. 1 is a schematic diagram of a configuration of a capsule endoscope system according to a first embodiment of the present invention.
Figure 2:
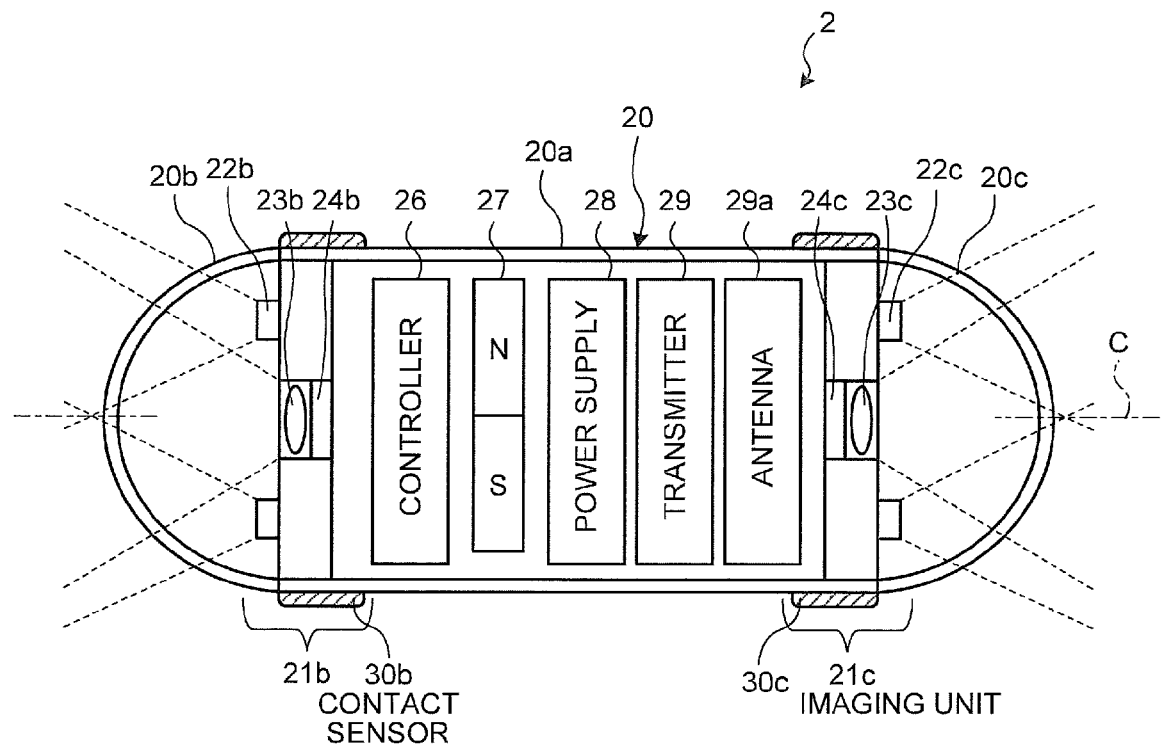
FIG. 2 is a schematic diagram of a configuration of a capsule endoscope according to the first embodiment of the present invention.
Figure 3:
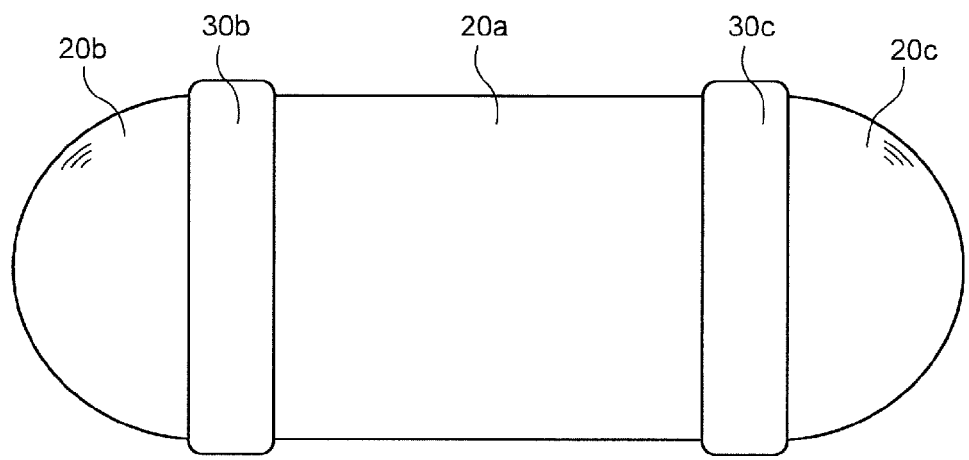
FIG. 3 is a diagram of an external configuration of the capsule endoscope according to the first embodiment of the present invention.
Figure 4:
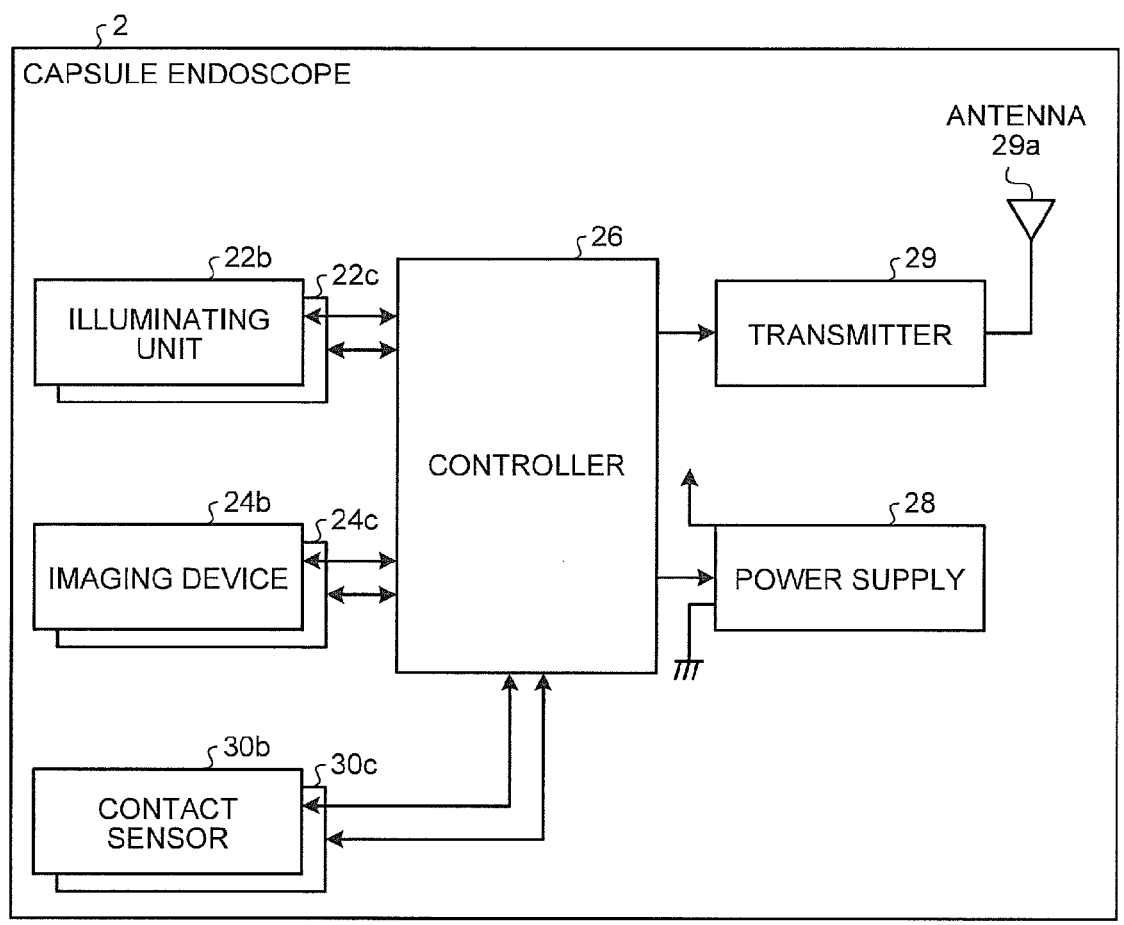
FIG. 4 is a block diagram of a configuration of the capsule endoscope according to the first embodiment of the present invention.

FIG. 1 is a schematic diagram of an overall configuration of a capsule endoscope system according to a first embodiment of the present invention. FIG. 2 is a schematic diagram of a configuration of a capsule endoscope that is used in the capsule endoscope system. FIG. 3 is a diagram of an external configuration of the capsule endoscope illustrated in FIG. 2. FIG. 4 is a block diagram of a functional configuration of the capsule endoscope.

As illustrated in FIG. 1, in a capsule endoscope system 11, a capsule endoscope 2 that is floatable in liquid 15 is introduced perorally into a subject 1 and, specifically, into a large intestine 14. While the capsule endoscope 2 in the large intestine 14 is guided, images of the inner wall of the large intestine 14 are acquired. The system includes a communication unit 3 that communicates wirelessly with the capsule endoscope 2 in the subject 1 via antennae $3a$ that are arranged on the body surface of the subject 1; a display unit that displays various types of information, such as in-vivo images of the subject 1, which are captured by the capsule endoscope 2; a magnetic field generator 5 that generates a magnetic field for guiding the capsule endoscope 2 in the subject 1; a power supply unit 6 that supplies power to the magnetic field generator 5; a moving unit 7 that moves the magnetic field generator 5; an input unit 8 that inputs various types of information, such as the type of the capsule endoscope 2 that is introduced; a storage unit 9 that stores various types of information, such as in-vivo images of the subject 1; and a controller 10 that controls the above-described components. The magnetic field generator 5, the power supply unit 6, and the moving unit 7 constitute a magnetic field generating device 17.

The capsule endoscope 2 is a capsule medical device that is formed in a size such that it can be introduced into the subject 1. The capsule endoscope 2 has a wireless communication function for external wireless communications. The capsule endoscope 2 also has an image capturing function for capturing in-vivo images of the subject 1. The capsule endoscope 2 sequentially captures in-vivo images of the inner wall of the large intestine 14 while moving through the large intestine 14 using the effects of an external magnetic field. Every time in-vivo images are captured, the capsule endoscope 2 sequentially transmits wirelessly image signals that contain the acquired in-vivo images to the outside of the subject 1. The capsule endoscope 2 further includes contact sensors $30b$ and $30c$ (see FIGS. 2 to 4) that detect contact with the inner wall of the large intestine 14. The contact sensors $30b$ and $30c$ sequentially transmit wirelessly contact information indicating whether contact with the inner wall has occurred.

The communication unit 3 is connected to the antennae $3a$, which are arranged on the body surface of the subject 1. The communication unit 3 communicates wirelessly with the capsule endoscope 2 in the subject 1 via any one of the antennae $3a$. The communication unit 3 receives wireless signals and contact information from the capsule endoscope 2 via the antennae $3a$, performs a demodulation process on the received wireless signals and the contact information, and extracts the image signals, which are contained in the wireless signals, and the contact information. The communication unit 3 transmits the extracted image signals and the contact information to the controller 10.

The magnetic field generator 5 is constructed using a plurality of electric magnets. The magnetic field generator 5 generates a three-dimensional external magnetic field, such as a rotation magnetic field or a gradient magnetic field, using electric power that is supplied from the power supply unit 6. Specifically, the magnetic field generator 5 can generate at least a magnetic field that has a gradient with respect to the vertical direction. The magnetic field generator 5 applies an external magnetic field to the capsule endoscope 2 that is in the subject 1 who is lying on a bed 13. The effects of the external magnetic field cause a magnetic attraction with the magnet (permanent magnet) in the subject 1, which guides the capsule endoscope 2 to a desired site in the body.

The moving unit 7 is configured to move the magnetic field generator 5 relative to the subject 1 such that the external magnetic field, which is generated by the magnetic field generator 5, is applied to the capsule endoscope 2 in the subject 1. Specifically, an X-Y plane is set that is approximately parallel to the surface of the bed 13 on which the subject 1 lies. The moving unit 7 moves the magnetic field generator 5 to a coordinate position on the X-Y plane under the control of the controller 10. In this case, the moving unit 7 moves the magnetic field generator 5 such that the capsule endoscope 2 in the subject 1 is positioned in the three-dimensional space in which the external magnetic field is generated by the magnetic field generator 5.

The input unit 8 may be constructed using input devices, such as a keyboard, a mouse, and a joystick. In response to an input operation by a user, such as a doctor or a nurse, the input unit 8 inputs various types of information to the controller 10. The input unit 8 also functions as an operation means that manipulates control by the controller 10 based on the result of display by a display unit 4. Various types of information that the input unit 8 inputs to the controller 10 includes, for example, instruction information for instructions to the controller 10, patient information on the subject, and examination information on the subject. Particularly, information on the type (size or density) of the capsule endoscope 2 is input.

The controller 10 includes an image processor $10a$ that generates in-vivo images of the subject 1, a position calculator $10b$ that calculates the position of the capsule endoscope 2 in the subject 1, and a magnetic field generation controller $10c$ that controls the intensity of the magnetic field, which is generated by the magnetic field generator 5, by controlling the amount of power supplied from the power supply unit 6 to the magnetic field generator 5.

The image processor $10a$ receives the image signals, which are obtained by demodulating the wireless signals from the capsule endoscope 2, from the communication unit 3, performs predetermined image processes on the received image signals, and generates image information, which corresponds to the image signals, i.e., in-vivo images of the subject 1. A group of in-vivo images, which are generated by the image processor $10a$, is displayed on the display unit 4 and stored in the storage unit 9.

The position calculator $10b$ receives, from the communication unit 3, the receiving field intensity of each of the antennae $3a$ (for example, the top three receiving field intensities out of those of the antennae $3a$.) with which the communication unit 3 sequentially receives wireless signals from the capsule endoscope 2. The position calculator $10b$ calculates the current position of the capsule endoscope 2 in the subject 1, using, for example, trigonometry, based on the received receiving field intensities and the position information on the antennae $3a$. The controller 10 associates the current position information, which is calculated by the position calculator $10b$, with the in-vivo images of the subject 1, which are captured by the capsule endoscope 2 existing in the current position. The controller 10 uses the current position information for control, by the magnetic field generation controller 10c, for guiding the capsule endoscope in the direction in which the capsule endoscope 2 moves. The in-vivo images of the subject 1 and the current position information on the capsule endoscope 2, which are associated with each other by the controller 10, are displayed on the display unit 4 and stored in the storage unit 9.

The magnetic field generation controller 10c controls the intensity of the magnetic field, which is generated by the magnetic field generator 5, based on the input guidance instruction information, current position information, and contact information in order to perform guidance control on the capsule endoscope 2. The magnetic field generation controller 10c performs control for generating, for the capsule endoscope 2, a combined guidance magnetic field for a combination of guidance in the moving direction (horizontal direction), which is the direction of the lumen axis of the large intestine 14, using the current position information and guidance in the gravitational force direction, which is the direction of the lumen radius of the large intestine 14, using the contact information.

A configuration of the capsule endoscope 2 will be explained below with reference to FIGS. 2 to 4. As illustrated in FIGS. 2 and 3, the capsule endoscope 2 includes a capsule-shaped casing 20 that is formed using a cylindrical casing 20a and dome-shaped casings 20b and 20c. A pair of contact sensors 30b and 30c that detects contact with the inner wall of the large intestine 14 is provided on the outer surface of the capsule-shaped casing 20. The contact sensors 30b and 30c are formed like belts that surround the cylindrical casing 20a at both end portions of the cylindrical casing 20a, and are constructed using pressure sensors that detect the pressure of the inner wall that is in contact with the capsule-shaped casing 20. The number of contact sensors 30b and 30c is not limited to two. One or three or more contact sensors may be used. In other words, it is satisfactory if contact sensors are used that can detect, without fail, contact with the inner wall of the large intestine 14 while the capsule endoscope 2 is in any posture.

The capsule-shaped casing 20 contains imaging units 21b and 21c that are provided at both ends of the capsule-shaped casing 20 in the direction of the cylinder axis C and that capture in-vivo images of the subject 1; a magnet 27 that is constructed using a permanent magnet, which causes attraction in accordance with the external magnetic field that is generated by the magnetic field generator 5; a power supply 28 that is constructed using a battery; a transmitter 29 and an antenna 29a that perform wireless communications with the external communication unit 3; and a controller 26 that controls the components of the capsule endoscope 2.

The specific gravity value of the capsule endoscope 2 is set to a value around a value less than the specific gravity value of the liquid 15, such as water to be supplied to the large intestine 14. If the liquid 15 is water, the specific gravity value of the capsule endoscope 2 is set to a value around a value less than 1. The center of gravity of the capsule endoscope 2 is set at approximately the center of the capsule-shaped casing 20 and is not significantly decentered. This is for inhibiting the capsule endoscope 2 from keeping a stable posture in the gravitational force direction in the liquid 15 and for enabling the capsule endoscope 2 to be guided easily along with the magnet 27 without inducing a large drag against the guidance magnetic field from the outside.

The capsule-shaped casing 20 is a casing having a shape like a capsule, which is formed in a size such that it can be introduced into the subject 1. Both open ends of the cylindrical casing 20a are sealed with the dome-shaped casings 20b and 20c, which have a shape like a dome, that keep the capsule-shaped casing 20 water-tight. The dome-shaped casings 20b and 20c are optical domes that are transparent with respect to light of a predetermined wavelength band (for example, visible light). In contrast, the cylindrical casing 20a is a nearly-nontransparent casing.

The imaging units 21b and 21c are configured to capture in-vivo images of the subject 1. The imaging units 21b and 21c include illuminating units 22b and 22c, optical systems such as condenser lenses 23b and 23c, and imaging devices 24b and 24c that are constructed using CCDs. The illuminating units 22b and 22c illuminate an object (specifically, the inner wall of the large intestine 14) through the dome-shaped casings 20b and 20c. The optical systems, which include the condenser lenses 23b and 23c, focus the light reflected from illuminated object, form optical images of the subject on the light receiving surfaces of the imaging devices 24b and 24c, and send the photoelectrically converted signals to the controller 26. The controller 26 generates in-vivo images by performing predetermined signal processes on the photoelectrically converted signals and transmits the in-vivo images to the outside of the subject 1 via the transmitter 29 and the antenna 29a.

The transmitter 29 transmits wirelessly the in-vivo images and the contact information via the antenna 29a, which is constructed using a coil antenna, under the control of the controller 26.

As illustrated in FIG. 4, the controller 26 controls the components of the capsule endoscope 2, i.e., the illuminating units 22b and 22c, the imaging devices 24b and 24c, the contact sensors 30b and 30c, and the transmitter 29. The controller 26 controls the timing at which the illuminating units 22b and 22c emit light and the amount of light to be emitted, controls the timing at which the imaging devices 24b and 24c capture images and the exposure time, receives signals of in-vivo images of the subject 1, performs the predetermined signal processes on the in-vivo image signals, and performs control for transmitting the signals wirelessly from the transmitter 29. Upon receiving a signal indicating contact with the inner wall from the contact sensors 30b and 30c, the controller 26 transmits contact information indicating the contact to the outside via the transmitter 29. The controller 26 may perform control for activating the contact sensors 30b and 30c when the capsule endoscope 2 has reached the large intestine 14. The controller 26 may perform control for transmitting contact information, which indicates contact with the inner wall, when contact with the inner wall occurs, or may perform control for constantly transmitting information indicating whether contact with the inner wall is occurring as, for example, binary information.

The power supply 28 is constructed using a switch circuit and a button battery. Under the control of the controller 26, the power supply 28 supplies power to the components of the capsule endoscope 2 when the switch circuit turns on the power supply 28. Furthermore, the controller 26 may have a pausing mode in which processes, such as the imaging process and contact detection, are not performed until predetermined conditions, for example, elapse of a predetermined time or reaching a predetermined position, are satisfied.

Figure 5:
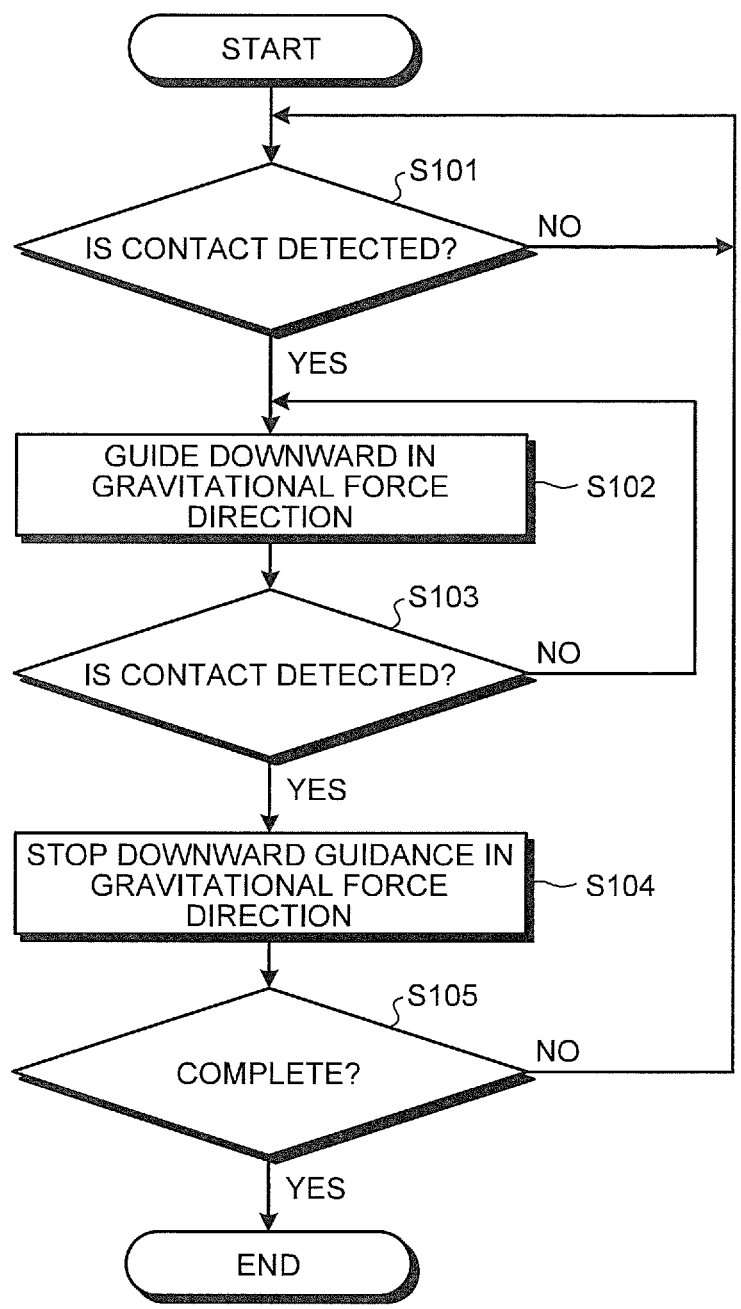
FIG. 5 is a flowchart of a procedure of a control process for guiding the capsule endoscope in the gravitational force direction, which is performed by a magnetic field generation controller, in a case where the specific gravity of the capsule endoscope according to the first embodiment of the present invention is less than that of liquid.
Figure 6:
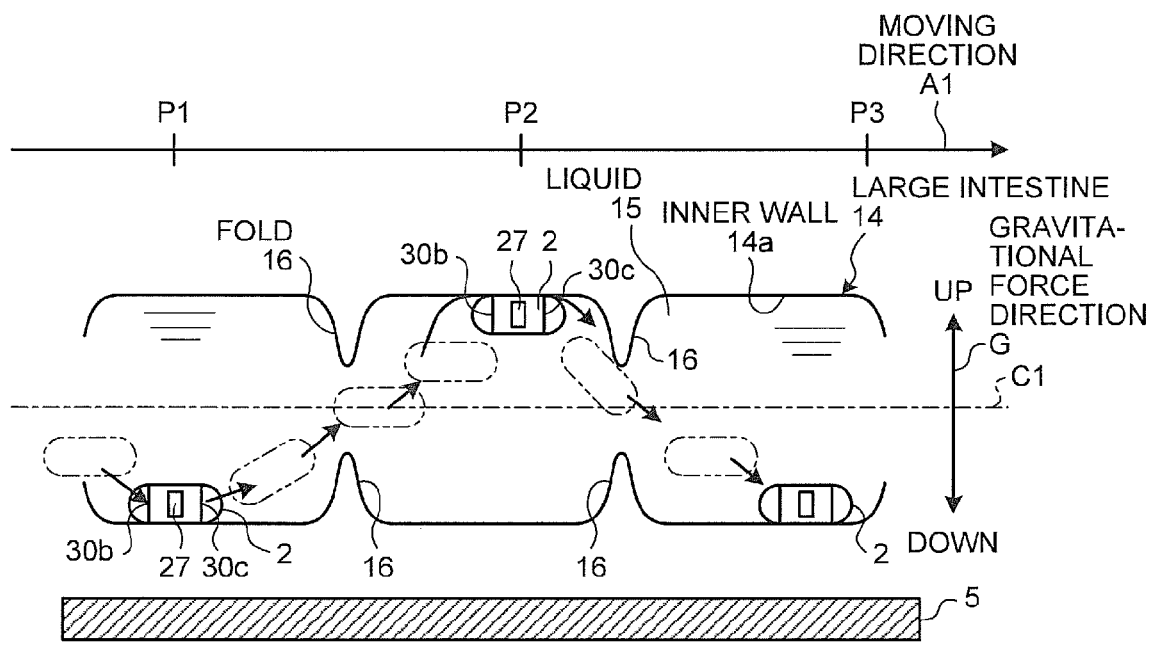
FIG. 6 is a schematic diagram representing an example of the guidance control that is performed by the magnetic field generation controller according to the first embodiment of the present invention.

A control process for guidance in the gravitational force direction, which is performed by the magnetic field generation controller 10c, in a state where the capsule endoscope 2 is located in the liquid 15 in the large intestine 14 will be explained below with reference to FIGS. 5 and 6. As illustrated in FIG. 5, first, the magnetic field generation controller 10c determines whether the capsule endoscope 2 has been brought into contact with an inner wall 14a of the large intestine 14 based on the contact information from the contact sensors 30b and 30c (step S101). In this initial determination process, because the specific gravity of the capsule endoscope 2 is less than the specific gravity of the liquid 15, the capsule endoscope 2 is being in contact with the inner wall 14a of the large intestine 14 on the upper side in the gravitational force direction G (vertically upper side) if the large intestine 14 is filled with the liquid 15.

The magnetic field generation controller 10c then repeats the determination at step S101 until contact with the inner wall 14a is detected. When contact with the inner wall 14a is detected (YES at step S101), the magnetic field generation controller 10c performs control for guiding the capsule endoscope 2 downward in the gravitational force direction G (step S102) and then determines whether contact with the inner wall 14a is detected (step S103). When contact with the inner wall 14a is not detected (NO at step S103), the magnetic field generation controller 10c goes to step S102 and repeats the above-described control for downward guidance in the gravitational force direction G. In contrast, when contact with the inner wall 14a is detected (YES at step S103), the magnetic field generation controller 10c stops the control for downward guidance in the gravitational force direction G, which has been performed, (step S104) to allow the capsule endoscope 2 to move upward in the gravitational force direction G only due to the buoyancy of the capsule endoscope 2 itself. Thereafter, the magnetic field generation controller 10c determines whether to complete the guiding process (step S105). Unless the guiding process is completed (NO at step S105), the magnetic field generation controller 10c jumps to step S101 and repeats the above-described process for guidance in the gravitational force direction G. When the guiding process is completed (YES at step S105), the magnetic field generation controller 10c completes the control process.

The magnetic field generation controller 10c performs, in addition to the process for guidance in the gravitational force direction G, control for guidance in the horizontal moving direction A1 based on information on the current position of the capsule endoscope 2. Accordingly, the capsule endoscope 2 in the large intestine 14 moves in the moving direction A1 while repeating contact with the inner wall 14a on the upper side in the gravitational force direction G and the inner wall 14a on the lower side in the gravitational force direction G. In other words, the capsule endoscope 2 zigzags through the large intestine 14 in the moving direction A1, which is in the direction of the lumen axis C1 of the large intestine 14 (see the positions P1, P2, and P3 shown in FIG. 6). Therefore, images of the entire inner wall 14a of the large intestine 14 can be captured. In addition, the zigzagging enables crossing over folds 16 in the large intestine 14. Because it is satisfactory if the magnetic field generation controller 10c performs a combination of the control for downward guidance in the gravitational force direction G and the control for guidance in the moving direction A1, simple guidance control can be performed. In addition, control for upward guidance in the gravitational force direction G is not performed. This helps to reduce power consumption and make the device smaller.

The overall process for observing (examining) the large intestine 14 using the capsule endoscope system 11 will be explained below.

1) First, the subject 1 swallows beforehand a pre-treatment medial agent, such as an intestinal lavage solution, in order to clean the inside of the large intestine 14.

2) Thereafter, the capsule endoscope 2 is taken. The capsule endoscope 2 moves by peristalsis while observing the inside of the body. The pausing mode in which observation (image acquisition) is not performed may be set for a predetermined period or until the capsule endoscope 2 reaches a predetermined site.

3) When it is confirmed that the capsule endoscope 2 has reached the large intestine 14, for example, because the predetermined period has elapsed or through the observation images, the capsule endoscope 2 acquires in-vivo images of the large intestine 14 and contact information, which is obtained by the contact sensors 30b and 30c, under the guidance control for zigzagging in the large intestine 14, and transmits the in-vivo images and the contact information to the outside.

4) Around the time when the capsule endoscope 2 has reached the large intestine 14, the subject 1 appropriately takes the liquid 15, such as the intestinal lavage solution, such that the large intestine 14 is filled with the liquid 15.

5) After the capsule endoscope 2 has reached the large intestine 14, the subject 1 lies on his or her back on the bed 13, as illustrated in FIG. 1, and assumes a posture such that the large intestine 14 is approximately horizontal.

6) It is satisfactory if, regarding the magnetic field for moving the capsule endoscope 2 horizontally (the moving direction A1), the approximate position of the capsule endoscope 2 in the large intestine 14 is estimated according to the in-vivo images, which are acquired by the capsule endoscope 2, or according to the time period which the capsule endoscope 2 takes to pass through. The capsule endoscope 2 is then moved in accordance with the estimation. If the capsule endoscope 2 is at the ascending colon, a magnetic field for moving the capsule endoscope 2 upward in the body axis direction (the direction toward the head) is generated. If the capsule endoscope 2 is at the transverse colon, a magnetic field for moving the capsule endoscope 2 in the direction orthogonal to the body axis is generated. If the capsule endoscope 2 is at the descending colon, a magnetic field for moving the capsule endoscope 2 downward in the body axis direction is generated. Alternatively, it may be determined not to move further when the capsule endoscope 2 is continuously moved horizontally in a certain direction and accordingly no change can be seen in the acquired in-vivo images, and the capsule endoscope 2 may be moved horizontally in a different direction, the determination and moving of which are repeatedly performed.

Alternatively, the direction in which the capsule endoscope 2 moves may be determined by taking into consideration the current position information, which is calculated by the position calculator 10b, or in accordance with the following directions. The site in the large intestine at which the capsule endoscope 2 exists may be determined based on an appropriate combination of, for example, the elapsed time, the direction in which the capsule endoscope 2 is propelled, and the number of curves the capsule endoscope 2 has passed through.

EXAMPLES

1) It can be determined that the capsule endoscope 2 is at the ascending colon when the moving direction A1 is in the body axis upward direction and/or the capsule endoscope 2 has passed through no curves (hepatic flexure) and/or the time after the capsule endoscope 2 has reached the large intestine 14 is short.

2) It can be determined that the capsule endoscope 2 is at the transverse colon when the moving direction A1 is orthogonal to the body axis and/or the capsule endoscope has passed through a curve (hepatic flexure) once and/or the time after the capsule endoscope 2 has reached the large intestine 14 is about 10 minutes.

3) It can be determined that the capsule endoscope 2 is at the descending colon when the moving direction A1 is in the body axis downward direction and/or the capsule endoscope 2 has passed through a curve (hepatic flexure) twice and/or the time after the capsule endoscope 2 has reached the large intestine 14 is about 20 minutes.

In the first embodiment, the specific gravity of the capsule endoscope 2 is less than the specific gravity of the liquid 15 and, thus, the capsule endoscope 2 floats in the liquid 15. Alternatively, the specific gravity value of the capsule endoscope 2 may be around a value larger than the specific gravity value of the liquid 15 and the guidance of the capsule endoscope 2 in the gravitational force direction G may be only performed upwards relative to the gravitational force direction G so that the capsule endoscope 2 zigzags through the large intestine 14.

Figure 7:
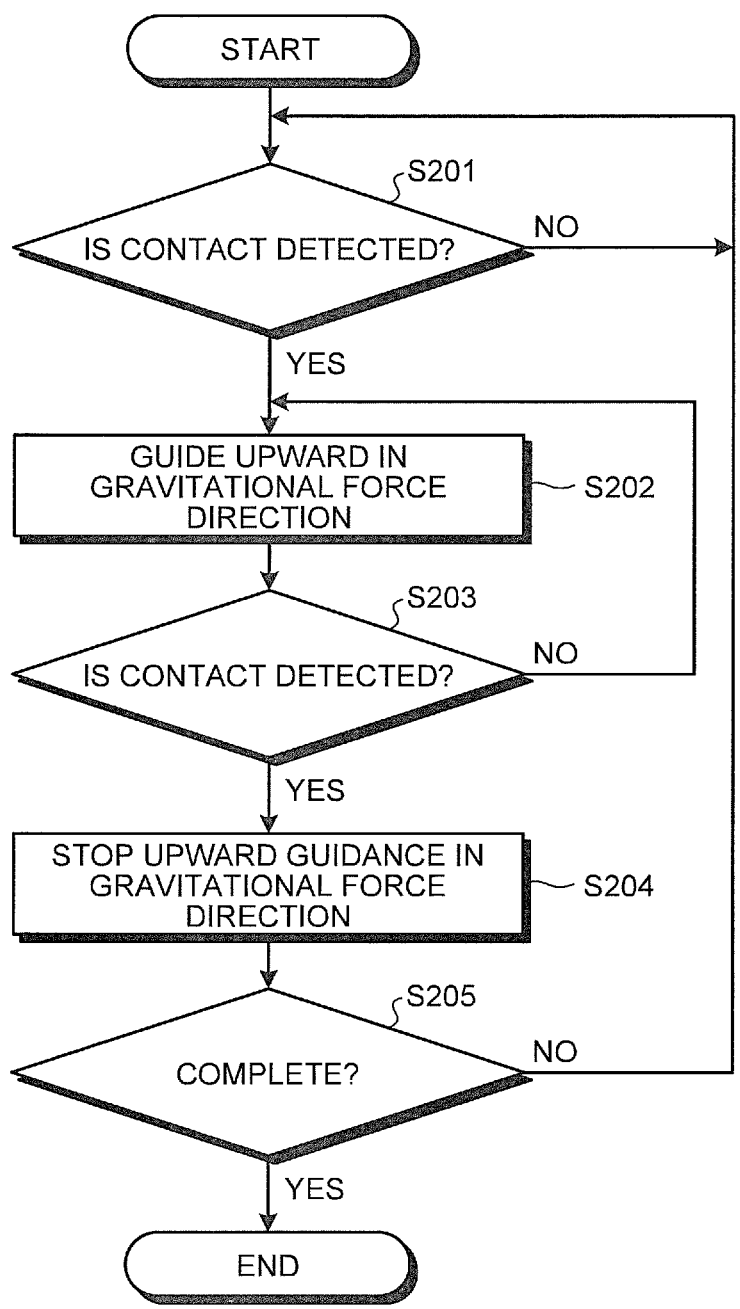
FIG. 7 is a flowchart of a procedure of a control process for guiding the capsule endoscope in the gravitational force direction, which is performed by a magnetic field generation controller, in a case where the specific gravity of the capsule endoscope according to the first embodiment of the present invention is larger than that of liquid.

FIG. 7 is a flowchart of a procedure of a control process for guidance in the gravitational force direction, which is performed by a capsule endoscope system according to a modification of the first embodiment. As illustrated in FIG. 7, the magnetic field generation controller 10c determines whether the capsule endoscope 2 has been brought into contact with the inner wall 14a of the large intestine 14 based on contact information from the contact sensors 30b and 30c (step S201). In the initial determination process, the specific gravity of the capsule endoscope 2 is larger the specific gravity of the liquid 15. Thus, if the large intestine 14 is filled with the liquid 15, the capsule endoscope 2 is being in contact with the inner wall 14a of the large intestine 14 on the lower side in the gravitational force direction G (orthogonally lower side).

Thereafter, the magnetic field generation controller 10c repeats the determination at step S201 until contact with the inner wall 14a is detected. When contact with the inner wall 14a is detected (YES at step S201), the magnetic field generation controller 10c performs control for guiding the capsule endoscope 2 upward in the gravitational force direction G (step S202). Thereafter, the magnetic field generation controller 10c determines whether further contact with the inner wall 14a is being detected (step S203). When contact with the inner wall 14a is not detected (NO at step S203), the magnetic field generation controller 10c goes to step S202 and repeats the control for upward guidance in the gravitational force direction G. In contrast, when contact with the inner wall 14a is detected (YES at step S203), the magnetic field generation controller 10c stops the control for upward guidance in the gravitational force direction G, which is performed (step S204) to allow the capsule endoscope 2 to move downward in the gravitational force direction G only by the gravity acting on the capsule endoscope 2. Thereafter, the magnetic field generation controller 10c determines whether to complete the guiding process (step S205). Unless the guiding process is completed, the magnetic field generation controller 10c jumps to step S201 and repeats the above-described process for guidance in the gravitational force direction G (NO at step S205). When the guiding process is completed (YES at step S205), the magnetic field generation controller 10c completes the process.

Also in this case, a combination of controls for guidance in the horizontal moving direction A1 allows the capsule endoscope 2 to zigzag through the large intestine 14 in the moving direction A1. Accordingly, images of the entire inner wall 14a of the large intestine 14 can be captured. In addition, the zigzagging allows crossing over the folds 16 in the large intestine 14. Because it is satisfactory if the magnetic field generation controller 10c performs a combination of the control for upward guidance in the gravitational force direction G and the control for guidance in the moving direction A1, easy guidance control can be performed. In addition, control for downward guidance in the gravitational force direction G is not performed. This helps to reduce power consumption and make the device smaller.

Second Embodiment

Subsequently, a second embodiment of the present invention will be explained below. In the first embodiment, the magnetic field generation controller 10c performs control for guidance in the gravitational force direction based on the contact information, which is acquired by the contact sensors 30b and 30c. In the second embodiment, it is determined whether the capsule endoscope 2 has been brought into contact with the inner wall 14a, using control result information about light control or exposure time control that is performed when the imaging units 21b and 21c acquire images. On the basis of the determination result, the magnetic field generation controller 10c performs control for guidance in the gravitational force direction.

Figure 8:
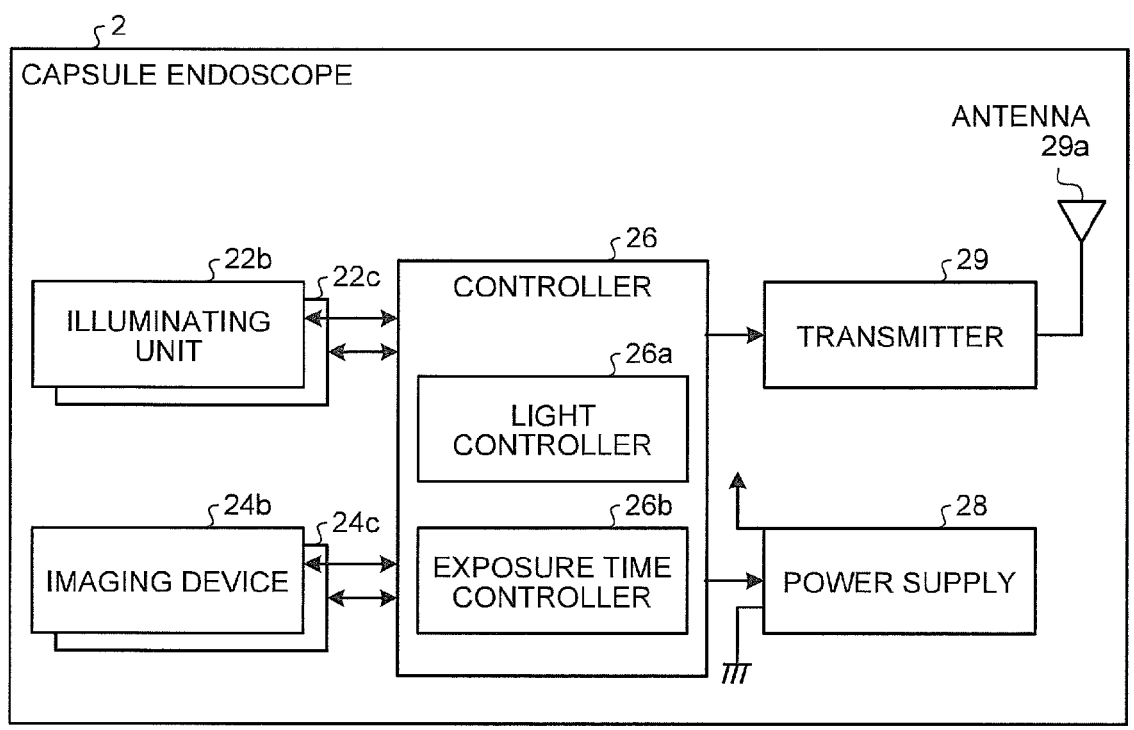
FIG. 8 is a block diagram of a configuration of a capsule endoscope according to a second embodiment of the present invention.

FIG. 8 is a block diagram of a configuration of a capsule endoscope of a capsule endoscope system according to the second embodiment of the present invention. In the capsule endoscope 2, the controller 26 includes a light controller 26a and an exposure time controller 26b. The light controller 26a and the exposure time controller 26b perform normal imaging control. The controller 26 transmits the control results to the controller 10 via the transmitter 29 and the antenna 29a, which is an aspect different from that of the first embodiment.

The light controller 26a performs control for adjusting the amount of light emitted from the illuminating units 22b and 22c. The exposure time controller 26b performs control for adjusting the exposure time in accordance with the luminance indicated by the acquired image information. Exposure control controls only the exposure time. This is because, the aperture for exposure is fixed in the case of the capsule endoscope 2 and thus the exposure amount is controlled only by controlling the exposure time.

The controller 26 transmits the light control information and/or the exposure information to the controller 10. The controller 26 has a contact detection function for determining whether the capsule endoscope 2 has been brought into contact with the inner wall 14a based on the light control information and the exposure information. The controller 26 then sends the determination results to the magnetic field generation controller 10c. For example, when the light control value is the exposure amount that is a predetermined value or less, it can be assumed that the capsule endoscope 2 is close to the inner wall 14a. Thus, it is then determined using the contact detection function that the capsule endoscope 2 has been brought into contact with the inner wall 14a. On the basis of the determination result, the magnetic field generation controller 10c performs control for guiding the capsule endoscope 2 in the gravitational force direction G, as in the case where the contact information is used. The communication unit 3 may be provided with the contact detection function. In this case, the communication unit 3 transmits the contact detection result to the magnetic field generation controller 10c.

In the second embodiment, it is determined whether the capsule endoscope 2 has been brought into contact with the inner wall 14a, not based on acquisition of contact information by the contact sensors 30b and 30c, but instead based on the light control information and/or the exposure information, which are results of control by the existing light controller 26a and/or the exposure time controller 26b. On the basis of the determination result, control for guidance in the gravitational force direction is performed. This helps to further reduce the size and weight of the capsule endoscope 2, for which reduction in size and weight is required.

In the second embodiment, it is determined whether the capsule endoscope 2 has been brought into contact with the inner wall 14a based on the light control information and/or the exposure information. Alternatively, it may be determined whether the capsule endoscope 2 has been brought into contact with the inner wall 14a by analyzing the acquired image information. For example, the image processor 10a may obtain an area with high luminance and an area with low luminance out of the areas in the acquired image and then determines whether the capsule endoscope 2 has been brought into contact with the inner wall 14a based on the luminance ratios between the areas. Specifically, when there is a bright portion in an area on the upper side in the image, it is assumed that area on the upper side is close to the inner wall 14a. In this case, it can be determined that the capsule endoscope 2 has been brought in contact with the inner wall 14a on the upper side in the gravitational force direction G. Also in this case, the contact sensors 30b and 30c are unnecessary. This helps further reduce the size of the capsule endoscope 2. Furthermore, the center of gravity of the capsule endoscope 2 may be adjusted such that the orthogonal relation in images, which are captured by the imaging devices 24b and 24c of the capsule endoscope 2, approximately coincide with the vertical direction of the gravitational force. In this case, the orthogonal relation is easily known from the captured images.

Third Embodiment

A third embodiment of the present invention will be explained below. In both of the first and second embodiments, the axis of the capsule endoscope 2, which moves through the large intestine 14, in the longitudinal direction is approximately horizontal. In the third embodiment, the magnetic field generation controller 10c performs guidance control for rotating the capsule endoscope 2 in a horizontal plane.

Figure 9:
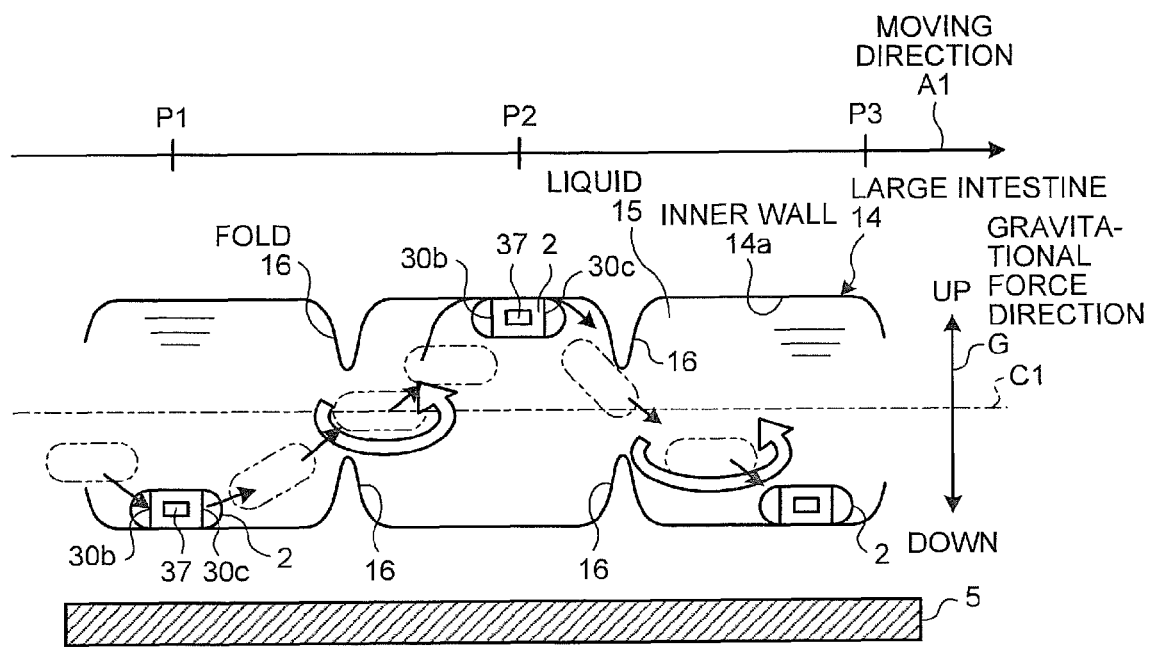
FIG. 9 is a schematic diagram representing an example of guidance control on a capsule endoscope, which is performed by a capsule endoscope system according to a third embodiment of the present invention.

FIG. 9 is a schematic diagram illustrating how the capsule endoscope 2 moves in the large intestine 14 in the case where the magnetic field generation controller 10c performs guidance control, including rotation guidance control, on the capsule endoscope 2. As illustrated in FIG. 9, as in the case of the first end second embodiments, the guidance control that is a combination of the control for guidance in the gravitational force direction G and the control for guidance in the moving direction A1 (the direction of the lumen axis C1 of the large intestine 14) is performed, so that the capsule endoscope 2 zigzags through the large intestine 14 (see the positions P1, P2, and P3 shown in FIG. 9). In the third embodiment, in addition to the guidance control, the capsule endoscope 2 is caused to rotate in the horizontal plane. In the rotation control, the capsule endoscope 2 may be rotated constantly or may be rotated intermittently.

In this case, because the capsule endoscope 2 that is floating in the liquid 15 (geometric center) has a center of gravity that is positioned at approximately the center of the capsule-shaped casing 20 and has a specific gravity approximately the same as that of the liquid 15, the capsule endoscope 2 can be rotated easily without applying a large guidance magnetic field. The capsule endoscope 2 according to the third embodiment may incorporate, instead of the magnet 27, a magnet 37 that is arranged such that its magnetization direction coincides with the direction of the cylinder axis C shown in FIG. 2 (a direction orthogonal to the radial direction of the capsule-shaped casing 20).

Using such rotation control allows the capsule endoscope 2 to acquire in-vivo images while missing fewer sites.

Fourth Embodiment

Figure 10:
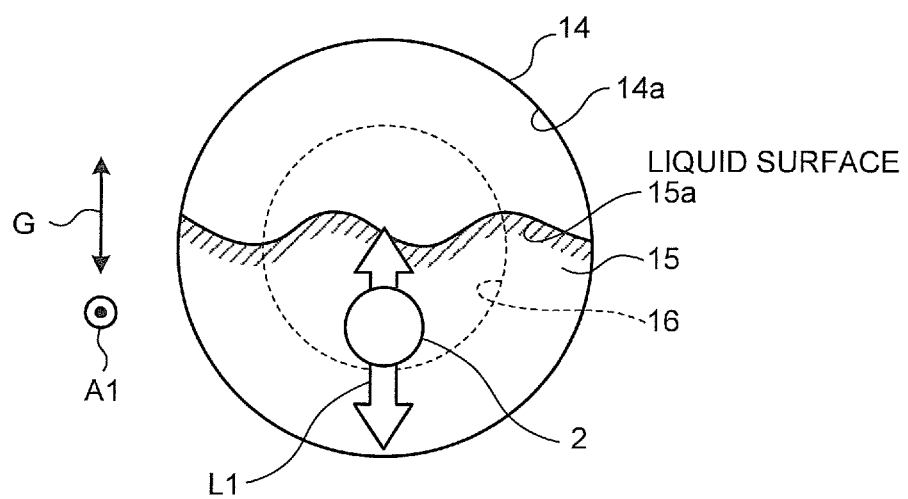
FIG. 10 is a lateral cross-sectional schematic diagram illustrating a range in which a capsule endoscope can be guided in the gravitational force direction in a case where the amount of liquid in the large intestine is small in the third embodiment of the present invention.
Figure 11:
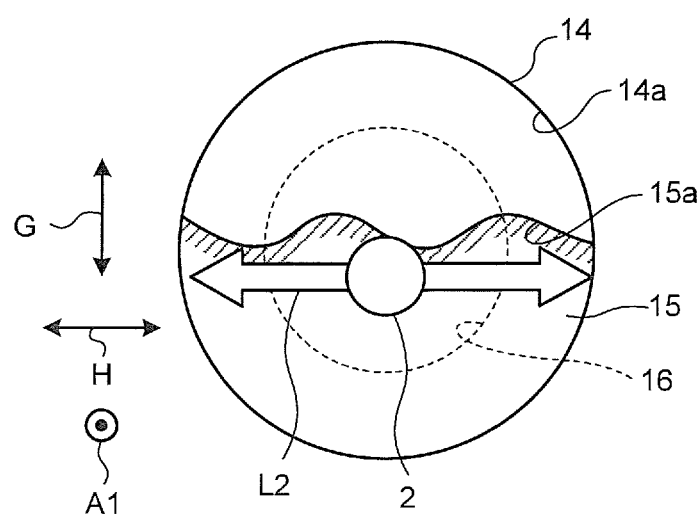
FIG. 11 is a lateral cross-sectional schematic diagram illustrating a range in which a capsule endoscope system according to a fourth embodiment of the present invention can guide a capsule endoscope horizontally.

A fourth embodiment of the present invention will be explained below. In each of the first to third embodiments, control for guidance in the gravitational force direction G is performed. As illustrated in FIG. 10, if the large intestine 14 is not fully filled with the liquid 15 in the large intestine 14 (see the position of a liquid surface 15a in the large intestine 14), a moving range L1 in the gravitational force direction G is less than the lumen diameter of the large intestine 14. In the fourth embodiment, the magnetic field generation controller 10c performs, not control for guidance in the gravitational force direction G, but control for guidance in the horizontal direction H. In other words, guidance control is performed such that the capsule endoscope 2 repeatedly moves back and forth in a direction approximately orthogonal to the direction in which the capsule endoscope 2 moves. In this case, as illustrated in FIG. 11, a range L2 in which the capsule endoscope 2 can move can be made approximately the same as the lumen diameter of the large intestine 14, as in the case where control for guidance in the gravitational force direction G is performed.

Fifth Embodiment

A fifth embodiment of the present invention will be explained below. In the fifth embodiment, the capsule endoscope 2 directs changing of the posture of the subject 1 such that the large intestine 14 is filled with the liquid 15.

Figure 12:
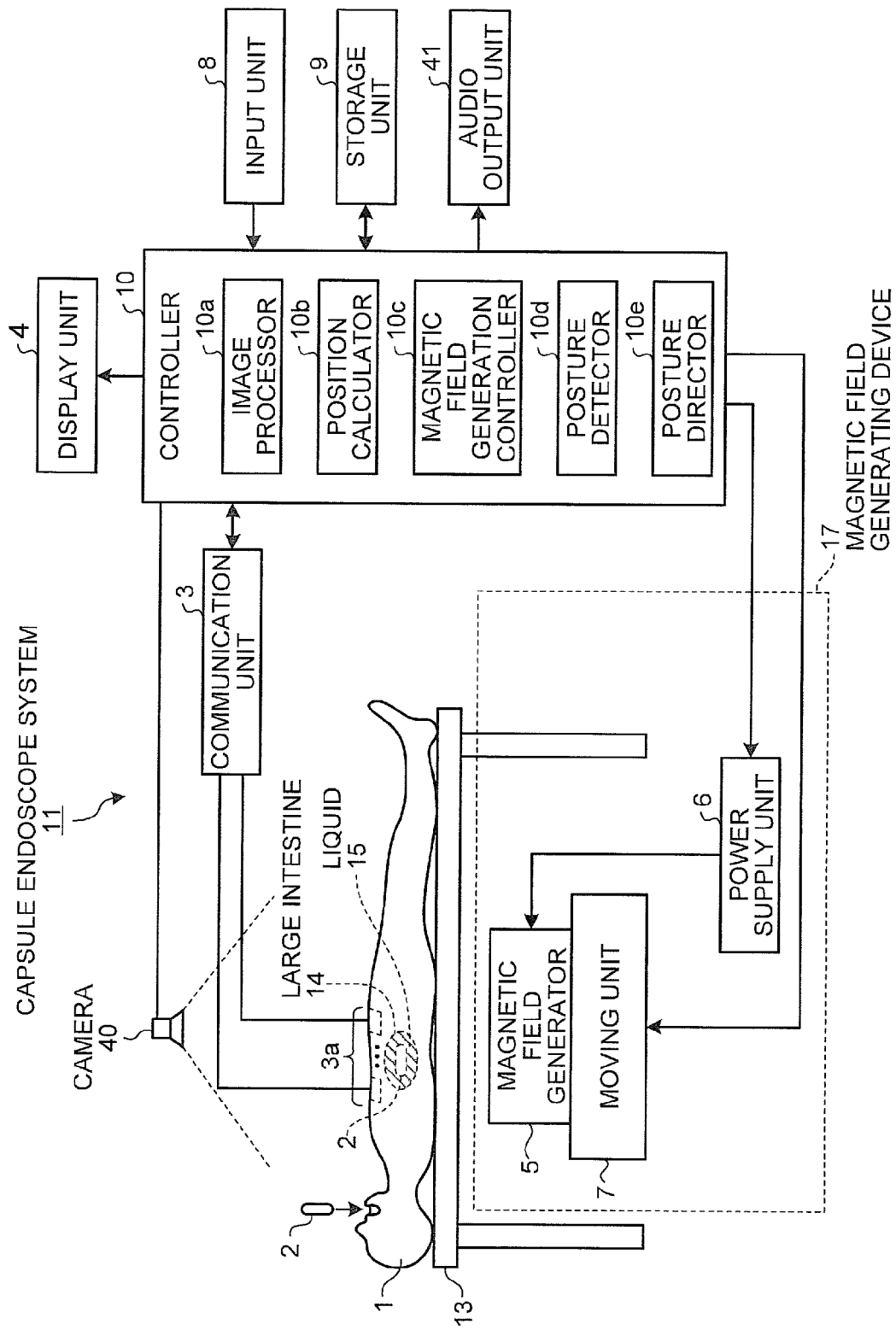
FIG. 12 is a schematic diagram of a configuration of a capsule endoscope system according to a fifth embodiment of the present invention.

FIG. 12 is a schematic diagram of a configuration of a capsule endoscope system according to a fifth embodiment of the present invention. As illustrated in FIG. 12, the capsule endoscope system 11 includes a camera 40 that captures images of the entire subject 1 and a posture detector 10d that detects the posture of the subject 1 based on the images, which are captured by the camera 40. The camera 40 and the posture detector 10d serve as a posture detector. The capsule endoscope system 11 further includes a posture director 10e. The posture director 10e generates instruction information for guiding the changing of the posture of the subject 1 based on the posture of the subject 1, which is detected by the posture detector 10d, and the site in the large intestine at which the capsule endoscope 2 is positioned, which is the site calculated by the position calculator 10b. The directing information may be output as audio guidance for changing the posture from an audio output unit 41.

If the subject 1 is in a posture in which the subject 1 lies on his or her back on the bed 13 as illustrated in FIG. 12 and the capsule endoscope 2 is at the ascending colon, the posture director 10e directs the subject 1 to turn to the right such that the right side of the subject faces down. Accordingly, the liquid 15 is concentrated on the ascending colon and the ascending colon is filled with the liquid 15 so that the capsule endoscope 2 can zigzag widely in the large intestine 14.

In the fifth embodiment, the camera 40 is used as a posture sensor. Alternatively, for example, the posture may be detected using a weight sensor or a temperature sensor that is arranged on the bed.

In the first to fifth embodiments, the capsule endoscope 2 includes two imaging units 21b and 21c. Alternatively, the capsule endoscope 2 may include only one imaging unit.

The contact sensors 30b and 30c are pressure sensors. Alternatively, the contact sensors 30b and 30c may be impedance sensors that detect variations in electrical resistance.

The position of the center of gravity of the above-described capsule endoscope 2 is at approximately the center of the capsule-shaped casing 20. Alternatively, for example, the position of the center of gravity may be shifted such that the axis of the capsule-shaped casing 20 in the longitudinal direction is oblique to the gravitational force direction or the direction of the center of gravity. In this case, it is preferable that the contact sensors be provided at positions such that contact with the inner wall 14a on the upper side and lower side in the gravitational force direction G can be detected without fail.

In each of the first to fifth embodiments, the case in which the capsule endoscope 2 is perorally taken is explained. Alternatively, if the purpose is to observe the large intestine, the capsule endoscope 2 can be introduced from the anus. In this case, the examination time can be shortened because the time for reaching the large intestine that is required if a peroral introduction is performed can be omitted. Furthermore, direct lavage can be performed on the large intestine if intestinal lavage is performed through the anus (colon hydrotherapy). Accordingly, intestinal lavage can be performed without fail. If the liquid in the large intestine is insufficient for dilation of the lumen, the liquid can be added through the anus, which means an optimum state in the lumen can be easily achieved.

As described above, the capsule endoscope system according to each of the embodiments is useful for observing the inside of the subject using a capsule endoscope. Particularly, the capsule endoscope system is suitable as a capsule endoscope system that can observe, under simple control, the inside of the lumen using a capsule endoscope that floats in liquid or is submerged in the liquid.

According to each of the above-described embodiments, when a capsule endoscope, which is introduced into the subject and floats in liquid or is submerged in the liquid in the subject, captures in-vivo images of a subject using at least one imaging unit, a magnetic field generation device performs guidance control in order to separate the capsule endoscope from the inner wall of the lumen through, for example, simple guidance in the upward direction or the downward direction relative to the gravitational force by causing the magnetic field generating device to generate an guidance magnetic field to apply to a magnet, which is provided in the capsule endoscope. Accordingly, the capsule endoscope can be propelled in the moving direction under simple control and the inside of the lumen can be entirely observed using the capsule endoscope that floats in liquid or is submerged in the liquid.

The above and other features, advantages and technical and industrial significance of this invention will be better understood by reading the following detailed description of presently preferred embodiments of the invention, when considered in connection with the accompanying drawings.

What is claimed is:

1. A capsule endoscope system for guiding a capsule endoscope that is introduced into a subject and floats in liquid or is submerged in the liquid in the subject, the capsule endoscope system comprising:
   a contact detector that detects contact with an inner wall of a lumen in the subject;
   a magnet which is equipped in the capsule endoscope;
   a magnetic field generating device that is provided at a position, which is fixed with respect to the magnet, and generates a guidance magnetic field to apply to the magnet from the outside of the subject; and
   a magnetic field generation controller that performs control for guidance in a direction in which the capsule endoscope moves, which is the direction of the axis of the lumen, and performs guidance control for separating the capsule endoscope from the inner wall of the lumen on based on the result of detection by the contact detector, wherein
   the magnetic field generation controller controls the magnetic field generating device to generate a guidance magnetic field for performing control for guidance in a direction in which the capsule endoscope moves horizontally,
   the magnetic field generation controller only controls, when a specific gravity of the capsule endoscope is less than that of a liquid supplied into the subject and when the contact detector detects the contact with the magnetic field generating device generating no guidance magnetic field for performing control for guidance downward in the gravitational force direction, the magnetic field generating device to generate a guidance magnetic field for performing control for guidance downward in the gravitational force direction,
   the magnetic field generation controller then moves, when the contact detector detects the contact with the magnetic field generating device generating the guidance magnetic field for performing control for guidance downward in the gravitational force direction, the capsule endoscope so that the capsule endoscope zigzags by repeatedly stopping the control for guidance downward in the gravitational force direction,
   the magnetic field generation controller only controls, when a specific gravity of the capsule endoscope is more than that of a liquid supplied into the subject and when the contact detector detects the contact with the magnetic field generating device generating no guidance magnetic field for performing control for guidance upward in the gravitational force direction, the magnetic field generating device to generate a guidance magnetic field for performing control for guidance upward in the gravitational force direction, and
   the magnetic field generation controller then moves, when the contact detector detects the contact with the magnetic field generating device generating the guidance magnetic field for performing control for guidance upward in the gravitational force direction, the capsule endoscope so that the capsule endoscope zigzags by repeatedly stopping the control for guidance upward in the gravitational force direction.

2. The capsule endoscope system according to claim 1, wherein the contact detector is provided on the outer surface of a casing of the capsule endoscope.

3. The capsule endoscope system according to claim 2, wherein the contact detector is a pressure sensor that detects a contact pressure.

4. The capsule endoscope system according to claim 2, wherein the contact detector is an impedance sensor.

5. The capsule endoscope system according to claim 1, further comprising at least one imaging unit which is equipped in the capsule endoscope that captures an in-vivo image of the subject,
   wherein the contact detector detects contact with the inner wall of the lumen based on light control information and exposure information that is obtained when the imaging unit captures an image.

6. The capsule endoscope system according to claim 1, further comprising at least one imaging unit which is equipped in the capsule endoscope that captures an in-vivo image of the subject, wherein the contact detector detects contact with the inner wall of the lumen based on information on luminance of an image, which is acquired by the imaging unit.

7. The capsule endoscope system according to claim 1, wherein the center of gravity of the capsule endoscope is at approximately the center of the capsule endoscope.

8. The capsule endoscope system according to claim 5, wherein the imaging unit is provided at one of the ends or each of the ends of the capsule endoscope in the direction of the axis of a cylindrical casing.

9. The capsule endoscope system according to claim 6, wherein the imaging unit is provided at one of the ends or each of the ends of the capsule endoscope in the direction of the axis of a cylindrical casing.

10. The capsule endoscope system according to claim 1, wherein the magnet is arranged such that a magnetization direction is orthogonal to the direction of the axis of a cylindrical casing.

11. The capsule endoscope system according to claim 1, wherein the magnet is arranged such that a magnetization direction is parallel to the direction of the axis of a cylindrical casing.

12. The capsule endoscope system according to claim 11, wherein the magnetic field generation controller performs control for generating a guidance magnetic field that causes the capsule endoscope to rotate by at least 180 degrees.

13. The capsule endoscope system according to claim 1, further comprising:
   a posture detector that detects a posture of the subject;
   a position detector that detects a site in the large intestine, in which the capsule endoscope is positioned; and
   a posture director that directs a change in the posture of the subject based on the posture of the subject, which is detected by the posture detector, and the site, which is detected by the position detector, such that the site, which is detected by the position detector, is at a vertically lower side.

* * * * *